US011298931B2

(12) United States Patent
Yadin et al.

(10) Patent No.: US 11,298,931 B2
(45) Date of Patent: Apr. 12, 2022

(54) INTERVERTEBRAL DISC REPLACEMENT

(71) Applicant: AGADA MEDICAL LTD., Kfar Vitkin (IL)

(72) Inventors: Amnon Yadin, Kfar Vitkin (IL); Isador Harry Lieberman, Plano, TX (US); Adi Dagan, Zichron Yaakov (IL); Yoram Fleischmann, Lehavot Hviva (IL)

(73) Assignee: AGADA MEDICAL LTD., Kfar Vitkin (IL)

( * ) Notice: Subject to any disclaimer, the term of this patent is extended or adjusted under 35 U.S.C. 154(b) by 171 days.

(21) Appl. No.: 16/506,504

(22) Filed: Jul. 9, 2019

(65) Prior Publication Data
US 2019/0329544 A1 Oct. 31, 2019

Related U.S. Application Data

(63) Continuation of application No. 15/234,923, filed on Aug. 11, 2016, now Pat. No. 10,390,959.
(Continued)

(51) Int. Cl.
*A61F 2/44* (2006.01)
*B33Y 80/00* (2015.01)
(Continued)

(52) U.S. Cl.
CPC .............. *B33Y 80/00* (2014.12); *A61F 2/442* (2013.01); *A61F 2/4425* (2013.01);
(Continued)

(58) Field of Classification Search
CPC .......... A61F 2/44; A61F 2/442; A61F 2/4425; A61F 2002/30289–30298;
(Continued)

(56) References Cited

U.S. PATENT DOCUMENTS 4,309,777 A 1/1982 Patil
4,759,769 A 7/1988 Hedman et al.
(Continued)

FOREIGN PATENT DOCUMENTS

CN 203861632 U 10/2014
DE 102013005398 B3 6/2014
EP 1652473 A1 5/2006

OTHER PUBLICATIONS

International Search Report issued in corresponding International Application No. PCT/US2017/046339 dated Oct. 23, 2017 (2 pages). [Cited in Parent].
(Continued)

*Primary Examiner* — Eduardo C Robert
*Assistant Examiner* — Michelle C Eckman
(74) *Attorney, Agent, or Firm* — Michele V. Frank; Venable LLP

(57) ABSTRACT

According to some embodiments of the invention, an intervertebral disc replacement includes a first layer having a lower surface for contacting a first vertebral bone, a second layer coupled to the first layer, the second layer comprising a plurality of compressible column springs, and a third layer coupled to the second layer, the third layer having an upper surface for contacting a second vertebral bone. Each of the plurality of compressible column springs comprises a plurality of stacked coils, and each of the plurality of stacked coils has a spring constant (K). At least one of the plurality of compressible column springs includes a first coil having a first spring constant and a second coil comprising a second spring constant, wherein the first spring constant is different from the second spring constant.

19 Claims, 13 Drawing Sheets

Related U.S. Application Data

(60) Provisional application No. 62/259,540, filed on Nov. 24, 2015.

(51) Int. Cl.
   *B29C 64/153* (2017.01)
   *A61F 2/30* (2006.01)
   *B33Y 10/00* (2015.01)
   *B33Y 50/02* (2015.01)
   *B29L 31/00* (2006.01)

(52) U.S. Cl.
   CPC .... *B29C 64/153* (2017.08); *A61F 2002/3023* (2013.01); *A61F 2002/30125* (2013.01); *A61F 2002/30143* (2013.01); *A61F 2002/30156* (2013.01); *A61F 2002/30172* (2013.01); *A61F 2002/30568* (2013.01); *A61F 2002/30621* (2013.01); *A61F 2002/30841* (2013.01); *A61F 2002/30891* (2013.01); *A61F 2002/30904* (2013.01); *A61F 2002/30917* (2013.01); *A61F 2210/0014* (2013.01); *A61F 2310/00023* (2013.01); *A61F 2310/00029* (2013.01); *B29L 2031/7532* (2013.01); *B33Y 10/00* (2014.12); *B33Y 50/02* (2014.12)

(58) Field of Classification Search
   CPC ............... A61F 2002/30563–30573; A61F 2002/30985; A61F 2002/3094–30942
   See application file for complete search history.

(56) References Cited

U.S. PATENT DOCUMENTS

| | | | |
|---|---|---|---|
| 5,108,438 A | 4/1992 | Stone | |
| 5,258,043 A | 11/1993 | Stone | |
| 5,458,642 A | 10/1995 | Beer et al. | |
| 5,827,328 A | 10/1998 | Buttermann | |
| 6,206,924 B1 | 3/2001 | Timm | |
| 6,770,094 B2 | 8/2004 | Fehling et al. | |
| 6,802,867 B2 | 10/2004 | Manasas et al. | |
| 7,563,284 B2 | 7/2009 | Coppes et al. | |
| 7,628,814 B2 | 12/2009 | Studer et al. | |
| 7,723,395 B2 | 5/2010 | Ringeisen et al. | |
| 7,731,753 B2 | 6/2010 | Reo et al. | |
| 7,758,645 B2 | 7/2010 | Studer | |
| 7,776,096 B2 | 8/2010 | Cauthen | |
| 8,057,546 B2 | 11/2011 | Studer et al. | |
| 8,246,680 B2 | 8/2012 | Betz et al. | |
| 8,398,712 B2 | 3/2013 | de Villiers et al. | |
| 9,241,808 B2 | 1/2016 | Sabatino | |
| 2002/0128714 A1* | 9/2002 | Manasas | B29C 64/153 |
| | | | 623/17.15 |
| 2005/0113924 A1* | 5/2005 | Buttermann | A61B 17/1671 |
| | | | 623/17.13 |
| 2005/0123581 A1 | 6/2005 | Ringeisen et al. | |
| 2005/0251260 A1 | 11/2005 | Gerber et al. | |
| 2006/0149381 A1 | 7/2006 | Kim | |
| 2006/0200239 A1 | 9/2006 | Rothman et al. | |
| 2006/0293752 A1 | 12/2006 | Moumene et al. | |
| 2007/0067038 A1 | 3/2007 | Studer et al. | |
| 2007/0288092 A1 | 12/2007 | Bambakidis | |
| 2009/0005874 A1* | 1/2009 | Fleischmann | A61F 2/442 |
| | | | 623/17.16 |
| 2009/0076613 A1 | 3/2009 | Biedermann et al. | |
| 2009/0157185 A1* | 6/2009 | Kim | A61F 2/442 |
| | | | 623/17.16 |
| 2010/0137990 A1 | 6/2010 | Apatsidis et al. | |
| 2011/0190904 A1* | 8/2011 | Lechmann | B29C 64/165 |
| | | | 623/23.61 |
| 2012/0016480 A1 | 1/2012 | Gerber et al. | |
| 2015/0045890 A1* | 2/2015 | Lefebvre | A61F 2/442 |
| | | | 623/17.15 |

OTHER PUBLICATIONS

Written Opinion issued in corresponding International Application No. PCT/US2017/046339 dated Oct. 23, 2017 (6 pages). [Cited in Parent].

* cited by examiner

SECTION B-B

INTERVERTEBRAL DISC REPLACEMENT

This application is a continuation of U.S. application Ser. No. 15/234,923 filed Aug. 11, 2016 and claims priority to U.S. Provisional Application No. 62/259,540 filed Nov. 24, 2015, the entire content of which is hereby incorporated by reference.

BACKGROUND

1. Technical Field

The field of the currently claimed embodiments of this invention relates to intervertebral disc replacements, and methods of producing intervertebral disc replacements.

2. Discussion of Related Art

The spine plays a prominent role in spinal cord and nerve root protection, weight bearing, and movement. The intervertebral disc is a core component of the spine and the spinal motion axis. The intervertebral disc acts in the spine as a stabilizer, and as a mechanism for force distribution between the vertebral bodies. Without the disc, collapse of the intervertebral space occurs in conjunction with abnormal joint mechanics and premature development of arthritic changes. However, existing intervertebral disc replacements often reduce compressive support, overload same level facet joints, and generate excessive wear particles from the bearing surfaces. Accordingly, there is a need for improved intervertebral disc replacements.

SUMMARY

According to some embodiments of the invention, an intervertebral disc replacement includes a first layer having a lower surface for contacting a first vertebral bone, a second layer coupled to the first layer, the second layer comprising a plurality of compressible column springs, and a third layer coupled to the second layer, the third layer having an upper surface for contacting a second vertebral bone. Each of the plurality of compressible column springs includes a plurality of stacked coils, and each of the plurality of stacked coils has a spring constant (K). At least one of the plurality of compressible column springs includes a first coil having a first spring constant and a second coil comprising a second spring constant, wherein the first spring constant is different from the second spring constant.

According to some embodiments, at least a second compressible column spring of the plurality of compressible column springs includes a coil having a third spring constant, wherein the third spring constant is different from at least one of the first and second spring constants. The disc replacement undergoes compression at a first rate when a compressive force is applied until a height of the disc replacement reaches a first predetermined value, and undergoes compression at a second rate as the height of the disc replacement is further reduced, wherein the second rate is less than the first rate.

According to some embodiments, each of the first layer and the third layer has a plurality of fixation mechanisms that engage the first vertebral bone or the second vertebral bone to fix the position of the intervertebral disc replacement with respect to the first and second vertebral bones. Each coil has a cross-section, and the cross-section of each coil has a flat lower surface and a flat upper surface that is parallel to the flat lower surface. Each cross-section has a maximum width, and according to some embodiments, each of the flat upper surface and the flat lower surface has a width that is at least 30% of the maximum width. According to some embodiments, each of the flat upper surface and the flat lower surface has a width that is at least 90% of the maximum width. According to some embodiments, each cross-section is substantially rectangular.

According to some embodiments, the plurality of compressible column springs are arranged in one or more concentric rings around the center of motion of the intervertebral disc replacement. At least one of the plurality of compressible column springs includes coils that are wound clockwise, and at least one of the plurality of compressible column springs includes coils that are wound counterclockwise. The intervertebral disc replacement mimics the compressive, extension, flexion, and rotational behavior of a human intervertebral disc.

According to some embodiments, the intervertebral disc replacement further includes a barrier attached to the first layer and the third layer and enclosing the second layer, wherein the barrier forms a fluid-tight seal with the first layer and the third layer.

According to some embodiments, each column spring has an outer circumference between about 3 mm and about 40 mm. According to some embodiments, the intervertebral disc replacement includes one or more of titanium, nitinol, cobalt chrome, and high density polycarbonate. According to some embodiments, each of the plurality of compressible column springs has a height that decreases when a compressive force is applied, and a structure that prevents the height from decreasing beyond a predetermined limit.

According to some embodiments, a difference between the first spring constant and the second spring constant is determined by a difference in at least one of a group consisting of a height of a cross section, a width of a cross-section, a pitch, and a material of the first coil and the second coil. According to some embodiments, the first layer, the second layer, and the third layer are one unitary piece.

According to some embodiments, the second layer includes a first plurality of compressible column springs attached to the upper surface of the first layer, a second plurality of compressible column springs attached to the lower surface of the third layer, and a fourth layer disposed between and attached to the first plurality of compressible column springs and the second plurality of compressible column springs. According to some embodiments, one or both of the first layer and the third layer has a height that varies.

According to some embodiments of the invention, a method of producing an intervertebral disc replacement includes forming, using a powder-based 3D printer, a first layer. The method further includes forming, using the powder-based 3D printer, a second layer on top of the first layer, the second layer comprising a plurality of compressible column springs. The method further includes forming, using the powder-based 3D printer, a third layer on top of the second layer, and removing unbound powder from the plurality of compressible column springs. Each of the plurality of compressible column springs includes a plurality of stacked coils, and each coil of each of the plurality of stacked coils has a spring constant. At least one of the plurality of compressible column springs is formed to include a first coil having a first spring constant and a second coil having a second spring constant, wherein the first spring constant is different from the second spring constant.

According to some embodiments, the method further includes, prior to forming the intervertebral disc replacement, obtaining at least one of x-ray, magnetic resonance imaging (MRI), computed tomography (CT), patient body mass above the disc replacement, and determining the angles of the end plates and the position of each of the plurality of compressible column springs and the spring constants of each of the plurality of stacked coils based on the obtained data to match a patient specific level lordosis and movement needs.

According to some embodiments, forming the second layer includes forming, using the powder-based 3D printer, a first plurality of compressible column springs attached to the upper surface of the first layer, forming, using the powder-based 3D printer, a fourth layer attached to the first plurality of compressible column springs, and forming, using the powder-based 3D printer, a second plurality of compressible column springs attached to the fourth layer and the lower surface of the third layer.

BRIEF DESCRIPTION OF THE DRAWINGS

Further objectives and advantages will become apparent from a consideration of the description, drawings, and examples.

DETAILED DESCRIPTION

Figure 1:
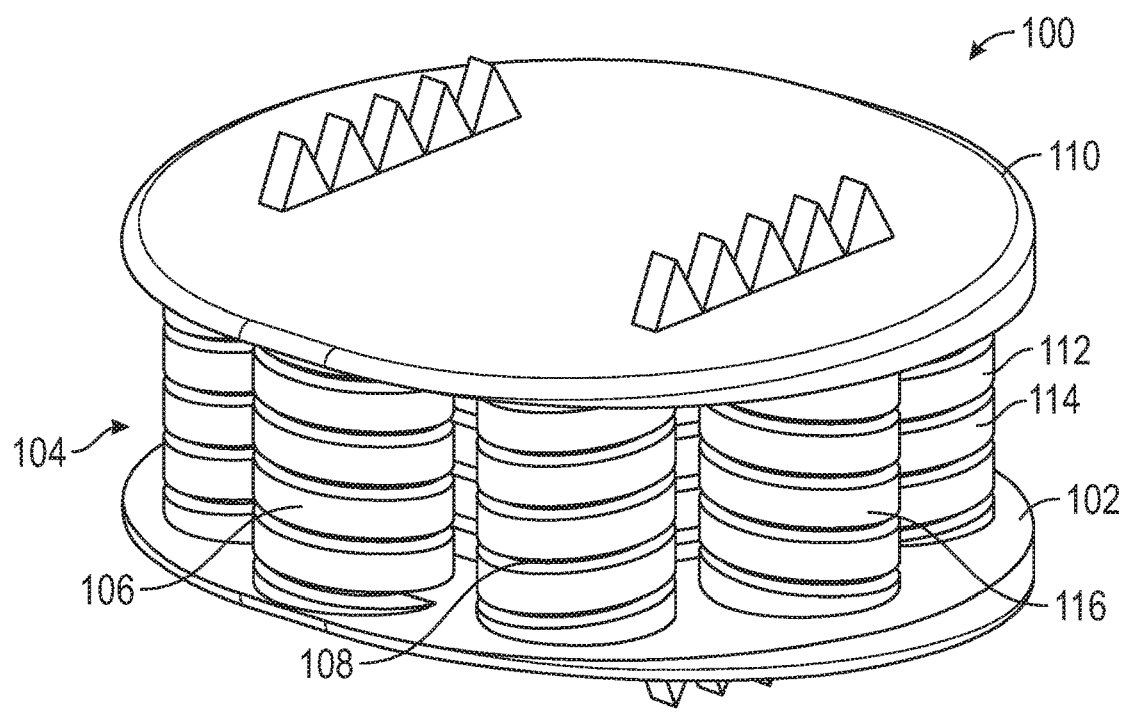
FIG. 1 shows a disc replacement according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The human intervertebral disc is composed of an inner gel-like matrix called the nucleus pulposus and an outer surrounding fibrous band called the annulus fibrosus. The disc's viscoelastic attributes provide shock absorbing capability that attenuate and transmit compressive and shear stresses. This force dampening protects the surrounding soft tissues and osseous structures from injurious loads. Furthermore, the disc's interposed position between adjacent vertebral bodies contributes to the spine's flexibility and provides mechanical restraints to excessive and deleterious spinal motion. In conjunction, the intervertebral disc, the vertebral bodies, and the facet joints form the "triple joint complex" that allows for physiologic spinal flexion, extension, lateral bending and rotation.

Chronic neck and low back pain are prevalent and costly diseases. Yearly, 15-20% of adults report at least one episode of neck pain, and close to half of these individuals seek care. Lifetime incidence of lumbar back pain (LBP) is reported to be 60-90% with annual incidence of 5%. Each year, 14.3% of new patient visits to primary care physicians are for LBP, and nearly 13 million physician visits are related to complaints of chronic LBP, according to the National Center for Health Statistics.

Annually, it is estimated that 11-14% of workers will experience some limitation in their work activities due to neck pain. In 1990, 400,000 industrial low back injuries resulted in disability in the United States. This number represents approximately 21% of injuries in the workplace and accounted for 31% of compensation payments.

A common cause of neck and lower back pain is a compromised intervertebral disc. Through various mechanisms, such as trauma, aging, or other disease processes, the intervertebral disc can become damaged. This damage results in some degree of pathologic change to the nucleus pulposus and the annulus fibrosis. Frequently, the nucleus pulposus becomes desiccated resulting in diminished load dampening properties and disc elasticity. This in turn leads to increased stresses on the annulus and facet joints, giving rise to the tearing of the annulus fibers and injury to facet cartilage. Further deterioration of disc components may lead to circumferential bulging of the disc, disc herniation, and facet joint arthritis. Pain receptors sense this deterioration and stimulate a pain response commonly referred to as axial neck or back pain. Pain primarily emanating from the disc injury is referred to as discogenic pain. Moreover, an extruded disc through direct compression of surrounding nerve roots/spinal cord and/or an inflammatory modulated mechanism can cause radicular symptoms (nerve pain) in the upper and/or lower extremities. Clinically, this underlying pathology presents as some combination of motor weakness, pain, and sensory dysthesia.

Commonly, surgeons perform a spinal arthrodesis to address the triple joint dysfunction and pain generated by the compromised intervertebral disc. During an arthrodesis the residual intervertebral disc is excised and an osteoconductive spacer is implanted and secured between the neighboring vertebrae by some combination of screws and plates/rods attached to the vertebra. With time the immobilized spacer forms a bone bridge, fusing adjacent vertebral bodies together. This procedure has provided for significant pain relief for many patients, but to the detriment of spinal motion near the fusion segment. Removal of motion at one segment alters the biomechanical environment, and necessarily magnifies the stresses at the triple joint complexes of adjacent joints. This adjacent joint mechanical overload accelerates deterioration, catalyzing the same pain generating process that arthrodesis was intended to resolve. This epiphenomenon is clinically described as adjacent joint disease. Therefore, with the passing of time, multilevel fusions are often indicated to treat the initial arthrodesis. Furthermore, arthrodesis is not without potential surgical complications, such as nonunion, infection, and injury to major blood vessels manipulated during the surgical approach.

To address the limitations of spinal arthrodesis, spinal intervertebral disc arthroplasty has gained popularity and has proven to be a viable alternative to arthrodesis for the treatment of discogenic spinal disease. Similar to arthrodesis, the injured intervertebral disc is excised, but instead of fusion of adjacent vertebra, a prosthetic disc is implanted that allows for preservation of motion. Many devices are currently marketed, both in the cervical and lumbar spine. Different devices can be primarily distinguished by their degree of constraint, type of bearing surfaces, geometry of bearing surfaces, and end plate interface.

Although current devices have demonstrated some success, overall results have left many practitioners and patients disappointed, especially with regards to same level and adjacent level facet disease. Such devices potentially suffer from various types of problems such as excessive unconstrained motion, distraction of disc space, inappropriate axes of rotation, wear debris, inadequate compression and shear stress attenuation, and surgical implantation and/or removal complications and risks. One type of existing replacement disc employs a ball-and-socket structure to allow some relative motion of the adjacent vertebrae. However, this disc design does not have a compressive component, and is therefore not able to act as a shock absorber. In addition, the bearing surface experiences significant friction due to the large load exerted on the disc. This friction can lead to pieces of the bearing surface and surrounding socket being sheared off, introducing loose debris into the area surrounding the disc. The loose debris can result in osteolysis (bone loss) and chronic inflammation at the implant site. Accordingly, opportunities exist for improvement on current disc replacement technology.

The disc replacement device described herein affords desirable characteristics and provides solutions to clinically relevant deficiencies in current spinal disc arthroplasty implants. The basic functional unit can be arranged in a unique geometric pattern that allows for spring-like mechanical properties. The unit can be composed of titanium and/or other biocompatible materials. This design stands in stark contrast to the "ball and socket" design of the vast majority of currently marketed products, and offers clear advantages to current technology.

First, a spring-like device in accordance with the principles of the invention demonstrates similar biomechanical properties to the viscoelastic properties of the native intervertebral disc. Thus, the device design can be readily manipulated to share more of the motion segment load, thereby achieving desirable compression and shear stress dampening. Clinically, this can lead to decreased incidence of facet and adjacent level disc disease, the preponderant reasons for current device failures. The disc can include a plurality of compressible springs. Each spring can be made of a plurality of coils, and the coils that make up a single spring may have different spring constants, such that the spring constant along the length of a single spring changes. Having a number of such springs in the disc replacement allows the disc replacement to have a different response to low compression loads compared to high compression loads, mimicking the behavior of a native disc.

In addition, the disc includes springs that are wound clockwise and springs that are wound counter-clockwise. By virtue of the clockwise or counter-clockwise winding of the springs, each spring can act as an antagonist to a strategically placed oppositely-wound spring. This allows for some rotation of the disc, but modulates unconstrained rotation. Thus, the clockwise and counter-clockwise springs are positioned to enable the disc to provide rotational characteristics similar to those of a native disc.

Second, the implant can be engineered to more precisely achieve the targeted instantaneous axes of rotation and spinal motion parameters. Accordingly, the load experienced by surrounding joints can be minimized, again reducing the likelihood of same level facet disease and adjacent level disc disease. As described above, the disc replacement can have a plurality of springs that can be finely tuned to mimic the compressive characteristics of a native disc. For example, certain areas of the plurality of springs can be designed to be more or less resistant to compression, by changing the spring constant of individual or even portions of springs. One can thus design regions of the disc known to experience greater forces to be less compliant, while less load-bearing areas can be more compressible.

The compressive lattice can also be designed to mimic the instantaneous axes of rotation that are characteristic of a native disc in its usual planes of motion. For motion at a specific spinal segment, one can imagine the superior vertebra rotating about a fixed point in the disc. However, since the superior and inferior vertebra can move relative to one another, this point within the disc can change. Thus, the term instantaneous axis of rotation is used to describe the axis of rotation at a particular time in the motion arc. The device in accordance with the principles of the invention can be designed in such a manner as to place the axis of rotation in an appropriate position, so the resulting moment can place lesser loads on the facet joints, leading to diminished pain and lessening the likelihood of clinical failure.

The disc replacement described herein can be designed to have one or more axes of rotation in the same anatomic region as a native intervertebral disc. For example, the column springs can be more compressible in certain areas to facilitate rotation at appropriate positions, and can inhibit rotation at inappropriate positions. The compressive and rotational qualities can also be fine-tuned depending on the intended anatomic position of the replacement disc. Cervical intervertebral discs and lumbar intervertebral discs can be designed differently to meet the particular motion profile, instantaneous axis of rotation characteristics, and load-bearing requirements of the target region of the spine.

The disc replacement has flexion, extension, and compression properties similar to those of a native disc. For example, when a patient with the disc replacement implanted in their spine bends forward, the anterior ends of the upper and lower layers of the disc move toward each other, while the posterior ends of the upper and lower layers spread apart from each, as is the case in a native disc. Similarly, during backward and lateral flexion, the upper and lower layers tilt with respect to each other in a manner that provides flexibility to the patient, but still provides shock-absorbing qualities that protect the adjacent vertebra.

Third, the device affords a near frictionless bearing surface, as opposed to the metal-polyethylene or metal-metal bearing surface of current implants. The design yields significantly less wear debris and minimizes the risk of osteolysis and chronic inflammation at the implant site. This also results in a decrease in the incidence of implant loosening, and a reduction in revision rates due to implant loosening.

Fourth, the disc replacement may be manufactured using a 3D printer, allowing it to be constructed to meet the exact, unique characteristics required for a given patient. The flexibility to augment implant dimensions and configurations via the 3D printing manufacturing process enables the device to address pre-operative sagittal plane deformity and reestablish normal lordosis. The overall dimensions of the disc replacement, including its height and width, as well as the shape of the bone-contacting surfaces, can be customized. In addition, the individual pieces can be structured to provide a compressive response like that of a native disc.

Finally, the intrinsic mechanical properties of the disc replacement provide rotational stability minimizing the likelihood of coronal plane deformity due to excessive rotational motion. As described above, the disc replacement is designed to promote desired rotation, and to limit or prohibit undesired rotation. Thus, the disc replacement can allow for rotational flexibility while preventing excessive rotational motion and the complications associated therewith.

Some embodiments of the current invention comprise a three-layer intervertebral disc replacement that allows for compression, bending, and rotation. FIG. 1 shows a disc replacement 100 that includes a first layer 102 having a lower surface for contacting a first vertebral bone. The disc replacement 100 includes a second layer 104 coupled to the first layer 102, the second layer 104 comprising a plurality of compressible column springs 106, 108. The disc replacement 100 includes a third layer 110 coupled to the second layer 104, the third layer 110 having an upper surface for contacting a second vertebral bone. Each of the plurality of compressible column springs includes a plurality of stacked coils, wherein each coil of each of the plurality of stacked coils has a spring constant (K). At least one of the plurality of compressible column springs includes a first coil 112 having a first spring constant and a second coil 114 having a second spring constant, wherein the first spring constant is different from the second spring constant.

The term "layer" is intended to have a broad meaning that should not be limited to a particular construct and/or embodiment. The term "layer" is generally used to refer to a region, area, portion, or section of the disc replacement.

The natural intervertebral disc is a mechanical entity with viscoelastic properties whose attributes are correlated to the speed by which force is exerted on it. In order to mimic this property with a compressible column spring, the compressible column spring is designed to have different K's along its length. This allows the disc replacement to respond differently to sudden impact versus gradually applied loads. The difference between resistance to impact and resistance to gradually built pressure is important to keep the vertebrae and the spinal column safe under impact while allowing freedom of movement under gradual application of pressure.

According to some embodiments of the invention, the intervertebral disc replacement has at least a second compressible column spring of the plurality of compressible column springs that includes a coil 116 having a third spring constant, wherein the third spring constant is different from at least one of the first and second spring constants. Because the spring constant of the second layer 104 can vary from column spring to column spring and also with a single column spring, the compressive response of the disc replacement can be finely tuned over each cubic millimeter of the disc replacement.

According to some embodiments of the invention, the first layer 102 and third layer 110 have a thickness that varies such that the upper surface and lower surface of a single layer may not be parallel. This design of the layers provides patient specific lordosis and kyphosis. The disc replacement be asymmetric. The thickness of the layers themselves may not be constant, and the distance between the upper surface of the first layer and the lower surface of the third layer may vary. Further, the distance between the lower surface of the first layer and the upper surface of the third layer may also vary. This allows the disc replacement to have a specific geometric shape that fits the space that the natural disc once occupied. The design also allows for patient-specific as well as level specific range of motion with as close to natural as possible free movement and resistance to movement.

There are a variety of ways in which the spring constant of the plurality of coils can be varied. For example, the outer radius of the coils can be varied, as well as the inner radius. Thicker coils (thickness=outer radius−inner radius) will generally have a higher spring constant, while thinner coils will generally have a lower spring constant. The height of a cross-section of a coil can be varied, as well as the pitch of the coils that make up the column springs. The pitch is defined as the distance in between a column spring's adjacent coils. The spring constant can also be varied by varying the materials used to make the spring. For example, if one coil of the spring is made from a first material and another coil of the spring is made from a second material having different elastic and deformation properties, the two coils will have different spring constants even if their dimensions are the same.

Figure 2:
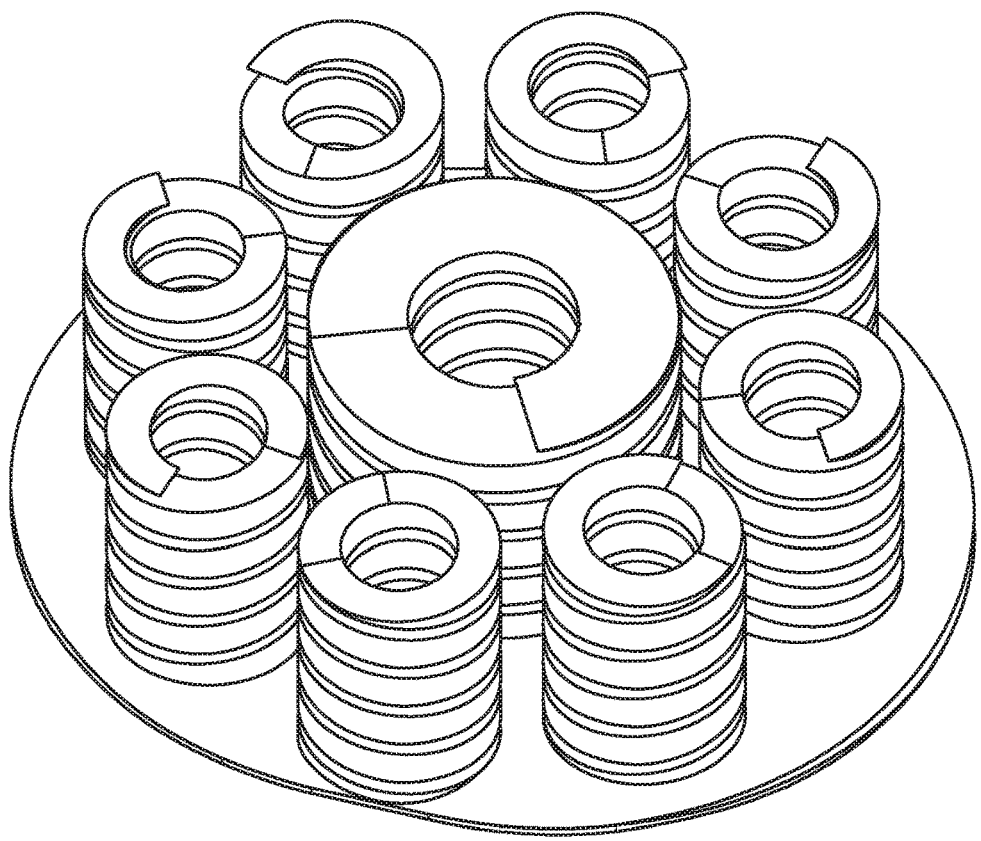
FIG. 2 shows the first and second layers of an intervertebral disc replacement according to some embodiments.

FIG. 2 shows the first and second layers of an intervertebral disc replacement according to some embodiments. In some embodiments, the plurality of compressible column springs are arranged in one or more concentric rings around the center of motion of the intervertebral disc replacement. This configuration can provide stability at the center of motion, while allowing the disc replacement to tilt in response to forces applied at the edge of the disk. According to some embodiments, the spring or springs closer to the center of motion may have a higher spring constant than the springs closer to the outer edges of the disc replacement. The embodiments of the invention are not limited to this configuration, however, and other strategic pattern can be employed to alter the compliance of the entire disc replacement. According to some embodiments of the invention, the disc replacement is designed to maximize the number of column springs in the second layer, without allowing any two column springs to come into contact with each other when the disc replacement is compressed or rotated.

Figure 3:
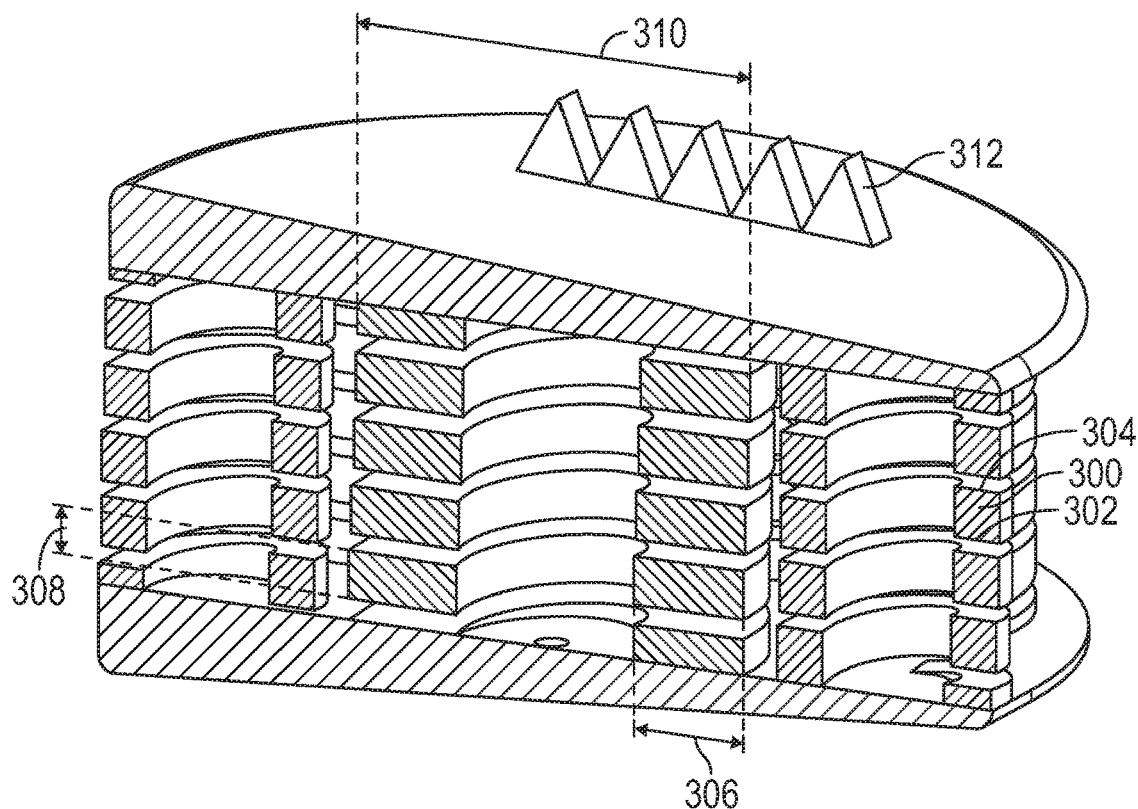
FIG. 3 shows a cross section of an intervertebral disc replacement.

FIG. 3 shows a cross section of an intervertebral disc replacement. As shown in FIG. 3, each coil has a cross section 300. According to some embodiments, the cross-section 300 of each coil has a substantially flat lower surface 302 and a substantially flat upper surface 304 that is substantially parallel to the substantially flat lower surface 302. The cross sections can be substantially rectangular. Each cross-section has a width 306 and a height 308. According to some embodiments, each column spring has an outer diameter 310 that is between about 3 mm and about 40 mm. The disc replacement can also have one or more fixation mechanisms 312 that engage the adjacent vertebra to fix the position of the disc replacement with respect to the vertebra. The fixation mechanisms can be spikes with tapered ends that contact the vertebra, though the embodiments of the invention are not limited to this design.

Figure 4:
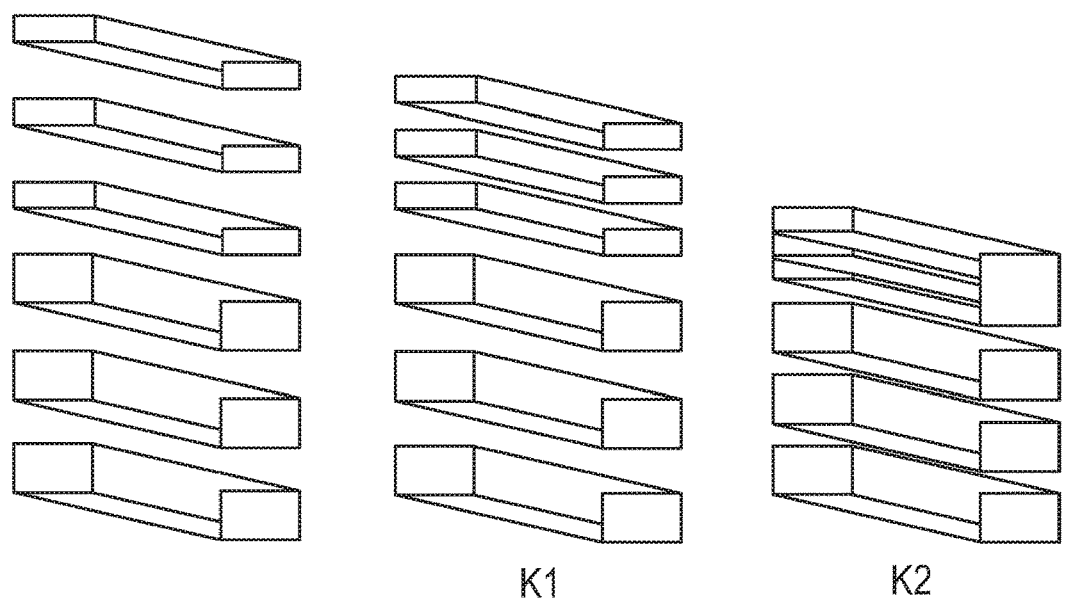
FIG. 4 illustrates the compression characteristics of the intervertebral disc replacement according to some embodiments.

FIG. 4 illustrates the compression characteristics of the intervertebral disc replacement according to some embodiments. The left-hand portion of FIG. 4 is a schematic illustration of a column spring having three upper coils with a first spring constant K1, and three lower coils with a second spring constant K2 that is greater than the first spring constant K1. When a compressive force is applied to the spring, the spring first compresses at a first rate determined primarily by the spring constant K1 of the upper springs. The lower springs undergo little or no compression. However, once the upper springs are mostly or fully compressed, the spring then compresses at a second rate that is determined primarily by the second spring constant, K2. The lower coils compress at this second rate until they, too, are fully compressed. Accordingly, the disc replacement undergoes compression at a first rate when a compressive force is applied until a height of the disc replacement reaches a first predetermined value, and then the disc replacement undergoes compression at a second rate as the height of the disc replacement is further reduced, wherein the second rate is less than the first rate. The plurality of springs by virtue of their coil design will impart a different compliance to the disc replacement at low loads compared to high loads. At low loads and slower rate of load application the disc replacement will be compliant with low stiffness, and for high loads or rapid rates of load application the disc replacement will be stiff or non-compliant.

Figure 5:
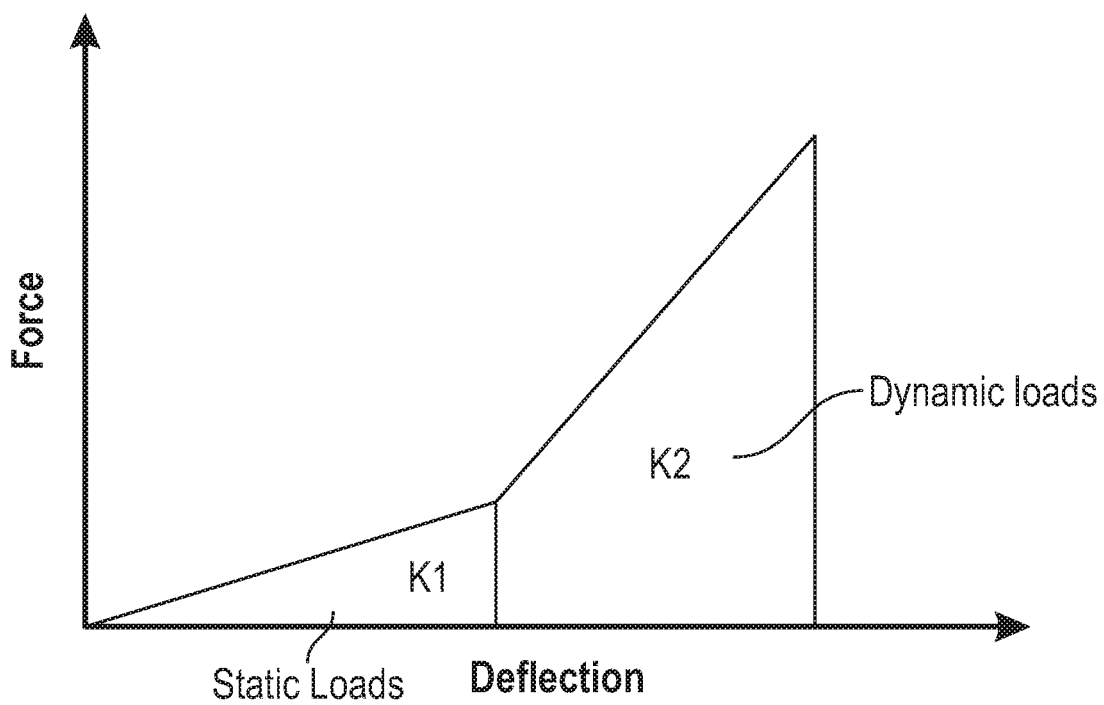
FIG. 5 shows a plot demonstrating the dependence of the compression rate on the applied load and two spring constants of one or more column springs.

The dependence of the compression rate on the applied load and two spring constants is illustrated in the plot in FIG. 5. Having two or more coils with different spring constants within a single column spring enables to the disc replacement to respond differently to static loads versus dynamic loads, enabling the intervertebral disc replacement to mimic the compressive, extension, flexion, and rotational behavior of a human intervertebral disc.

While FIGS. 4 and 5 illustrate a column spring with coils having two different spring constants, the embodiments of the invention are not limited to column springs with coils with just two spring constants. A column spring may have coils of three or more spring constants. Coils having the same spring constant may be grouped together within the column spring, or may be interspersed throughout the column spring. Further, when a compressive force is applied to a spring, coils within the spring having different spring constants may undergo compression at the same time, but at different rates.

Some column springs may only have coils of one spring constant, such that the spring constant along the full length of the column spring remains unchanged. Further, a disc replacement according to some embodiments may comprise a single column spring. The coils of the single column spring may have one or more spring constants. A disc replacement according to some embodiments may include a plurality of column springs, each having a single spring constant along its length. The spring constants of the plurality of column springs may all be the same, or may vary from column spring to column spring.

Figure 6:
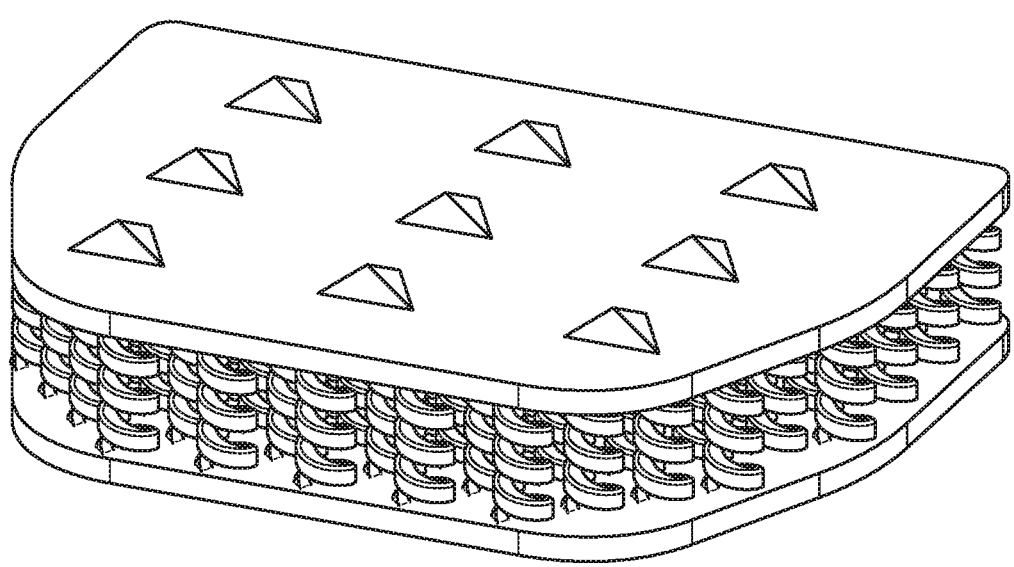
FIG. 6 shows an intervertebral disc replacement with beveled coils according to some additional embodiments.
Figure 7:
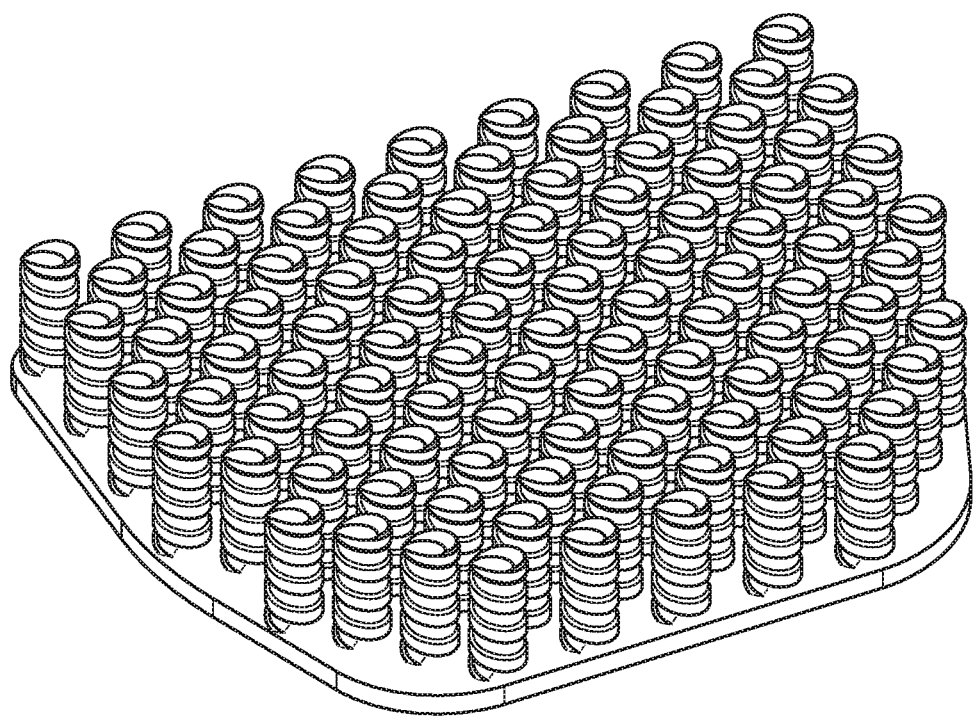
FIG. 7 shows the first and second layers of the disc replacement of FIG. 6.

FIG. 6 shows an intervertebral disc replacement with beveled coils according to some additional embodiments, and FIG. 7 shows the first and second layers of the disc replacement of FIG. 6. As shown in FIGS. 6 and 7, the coils of the column springs can have edges that are beveled or rounded. The coils have a cross-section with a flat upper surface and a flat lower surface, but the cross-section is not a rectangle like the cross-section 300 in FIG. 3. The cross-section has a maximum width, and each of the flat upper surface and the flat lower surface has a width that is at least 30% of the maximum width. According to some embodiments of the invention, each of the flat upper surface and the flat lower surface has a width that is at least 90% of the maximum width.

The flat upper and lower surfaces of the cross-sections of the coils creates a large surface area over which pressure can be distributed. If the coils are sufficiently compressed that they come into contact with each other, the forces applied by one coil on an adjacent coil are spread out over the flat surface, reducing the pressure at any single point. If the coils had a circular cross-section, each coil would contact its neighbor at only the top or bottom point of the cross-section, concentrating the force on that point. This potentially leads to wear and the release of debris as pieces of the spring break off due to excessive force. The design of the coils according to some embodiments of the invention prevents erosion of the coils by distributing forces over a larger surface area. When the column spring is uncompressed or partially compressed, a space exists between adjacent coils of a given spring, allowing the disc replacement to absorb shock exerted on the spine.

Figure 8:
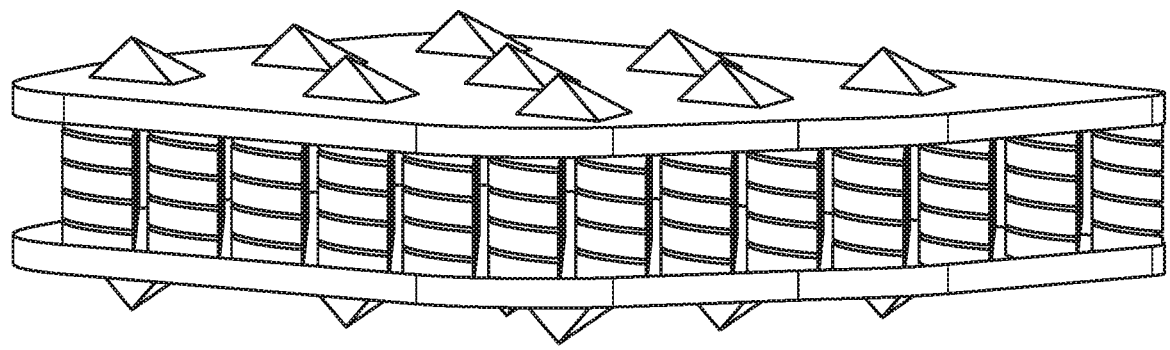
FIG. 8 shows a disc replacement wherein the coils of the column springs are maximally compressed.
Figure 9:
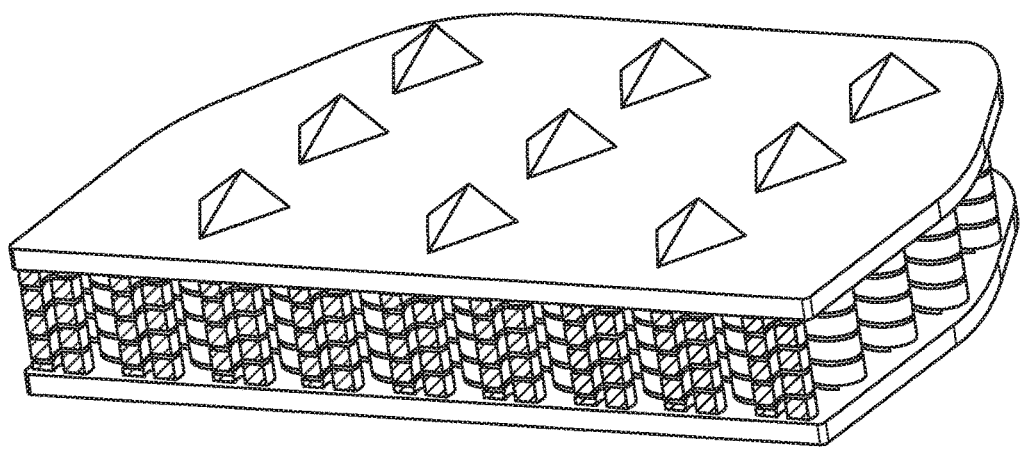
FIG. 9 shows a cross-section of the disc replacement shown in FIG. 8.
Figure 10:
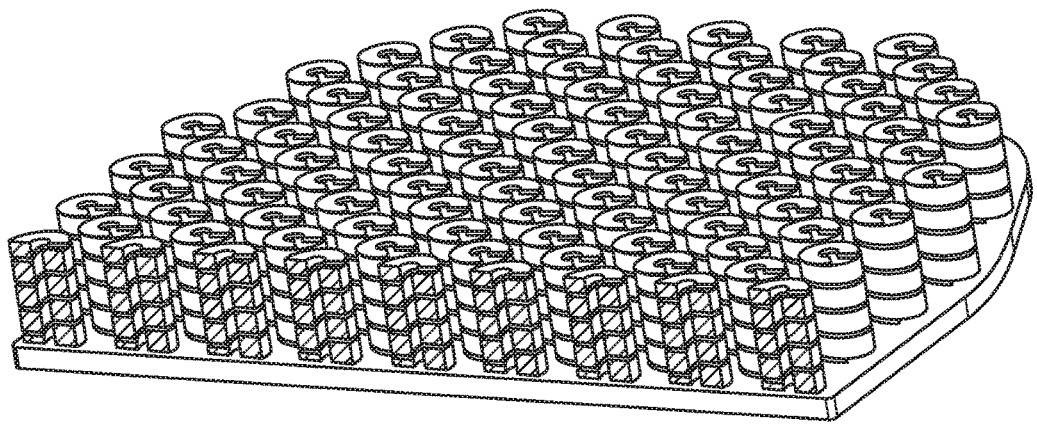
FIG. 10 shows the first and second layers of the disc replacement shown in FIGS. 8 and 9.

FIGS. 8-10 shows an intervertebral disc replacement undergoing complete compression. FIG. 8 shows how the coils of the column springs are maximally compressed. Each coil, with the exclusion of the upper-most and lower-most coils, comes into contact with the coils above and below it such that the distance between the first layer and the third layer reaches a minimum value, beyond which the disc replacement can no longer be compressed. The intervertebral disc replacement can thus be designed to have a minimum height that is pre-determined based on the patient's physiology.

Figure 11:
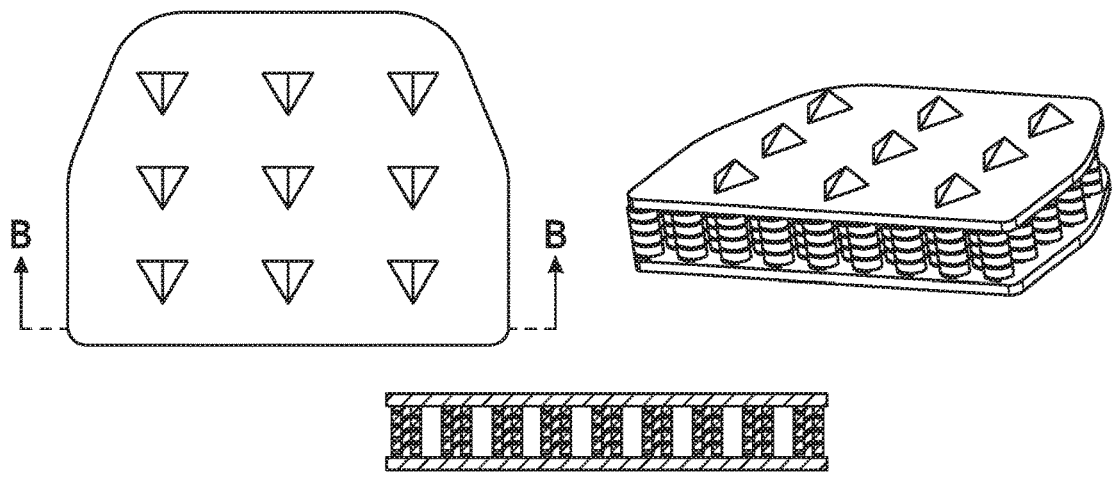
FIG. 11 shows additional images of a fully-compressed disc replacement.

FIG. 9 shows a cross-section of the disc replacement shown in FIG. 8. The cross-sections of the coils are visible, showing how the flat upper surface of each coil, with the exclusion of the upper-most coils, contacts the flat lower surface of the coil above it. This distributes the forces on each coil over a larger area, thereby reducing the pressure at any single point. FIG. 10 shows the first and second layers of the disc replacement shown in FIGS. 8 and 9. While FIG. 10 shows that all the column springs become maximally compressed at the same height, the embodiments of the invention are not limited to this concept. The minimum height of the disc replacement may be determined by the maximally-compressed height of one or more of the springs. Further, the minimum height might be different for different regions of the disc replacement. For example, the middle of the disc replacement may be compressible to a first minimum height, while the outer edges of the disc replacement may be further compressed to a second minimum height. FIG. 11 shows additional images of a fully-compressed disc replacement.

Figure 12:
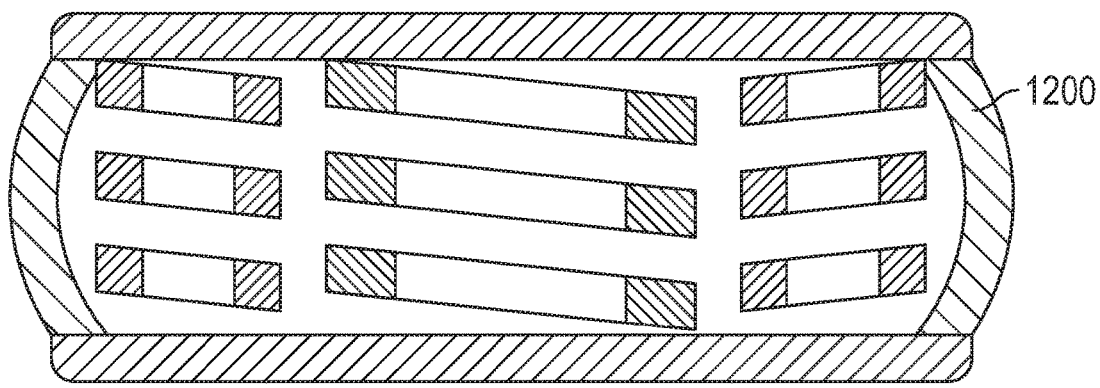
FIG. 12 shows a disc replacement including a barrier surrounding the second layer.

According to some embodiments of the invention, the intervertebral disc replacement includes a barrier disposed between the first layer and the third layer and surrounding the second layer. An example of a disc replacement including a barrier is shown in FIG. 12. The barrier 1200 surrounds the second layer, preventing the body from protruding or growing into the area of the column springs, thus protecting the springs from interference by the body. The barrier may be made of one or more of Gortex, polycarbonate, silastic, and any biocompatible membrane or tissue. The barrier may be made of a material that is impermeable and wear resistant. The barrier may be mechanically or chemically bonded to the upper and lower layers, or both mechanically and chemically bonded. The barrier may form a fluid-tight seal with the first layer and the third layer.

Figure 13:
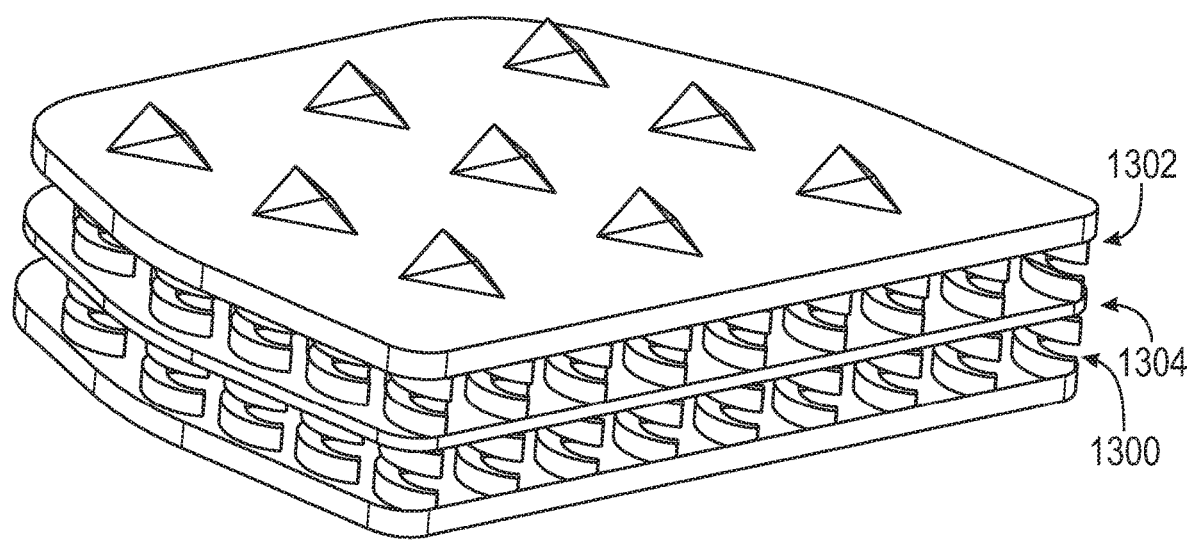
FIG. 13 shows an intervertebral disc replacement comprising two layers of column springs according to some embodiments of the invention.
Figure 14:
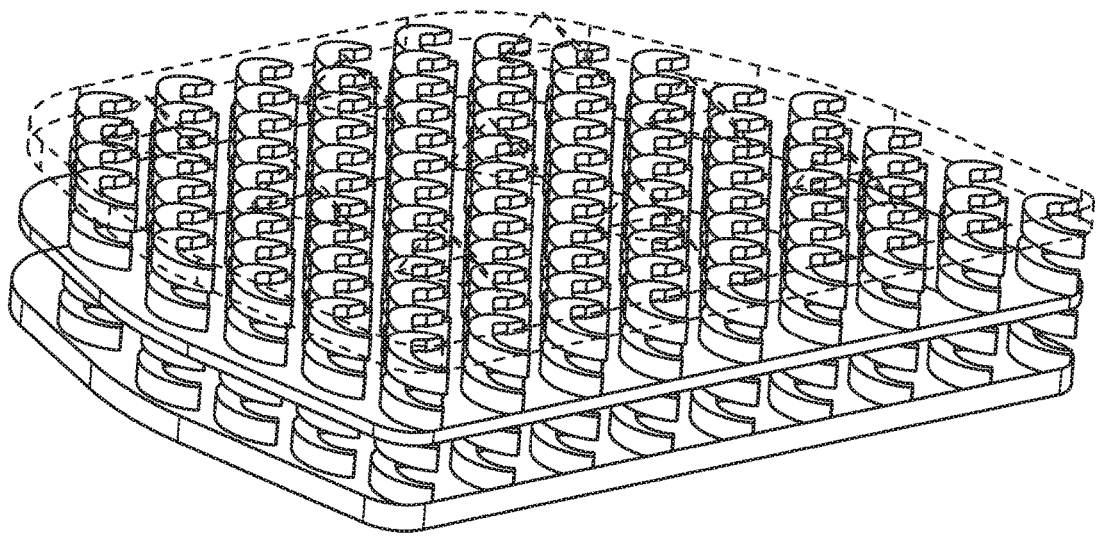
FIG. 14 shows the intervertebral disc replacement of FIG. 13 wherein the top plate has been rendered transparent.
Figure 15:
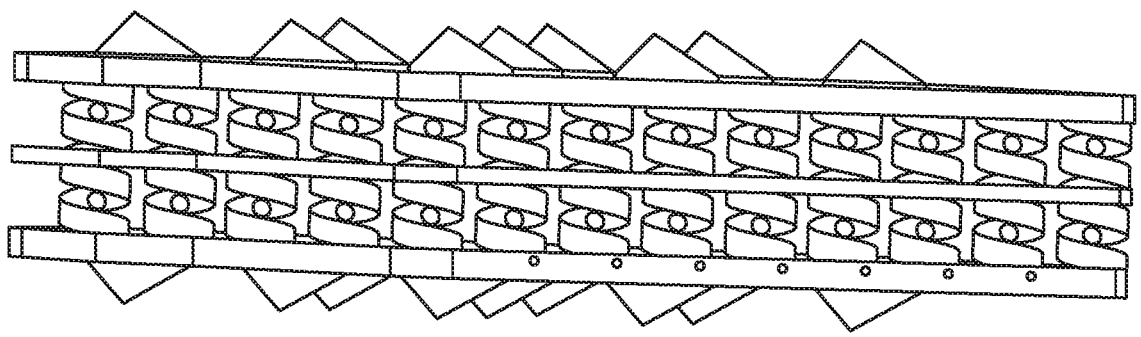
FIG. 15 shows a side view of the disc replacement shown in FIGS. 13 and 14.

An intervertebral disc replacement comprising two layers of column springs according to some embodiments of the invention is shown in FIG. 13. The second layer includes a first plurality of compressible column springs 1300 attached to the upper surface of the first layer, a second plurality of compressible column springs 1302 attached to the lower surface of the third layer, and a fourth layer 1304 disposed between and attached to the first plurality of compressible column springs 1300 and the second plurality of compressible column springs 1302. FIG. 14 shows the intervertebral disc replacement of FIG. 13 wherein the top plate has been rendered transparent. FIG. 15 shows a side view of the disc replacement shown in FIGS. 13 and 14.

Figure 16:
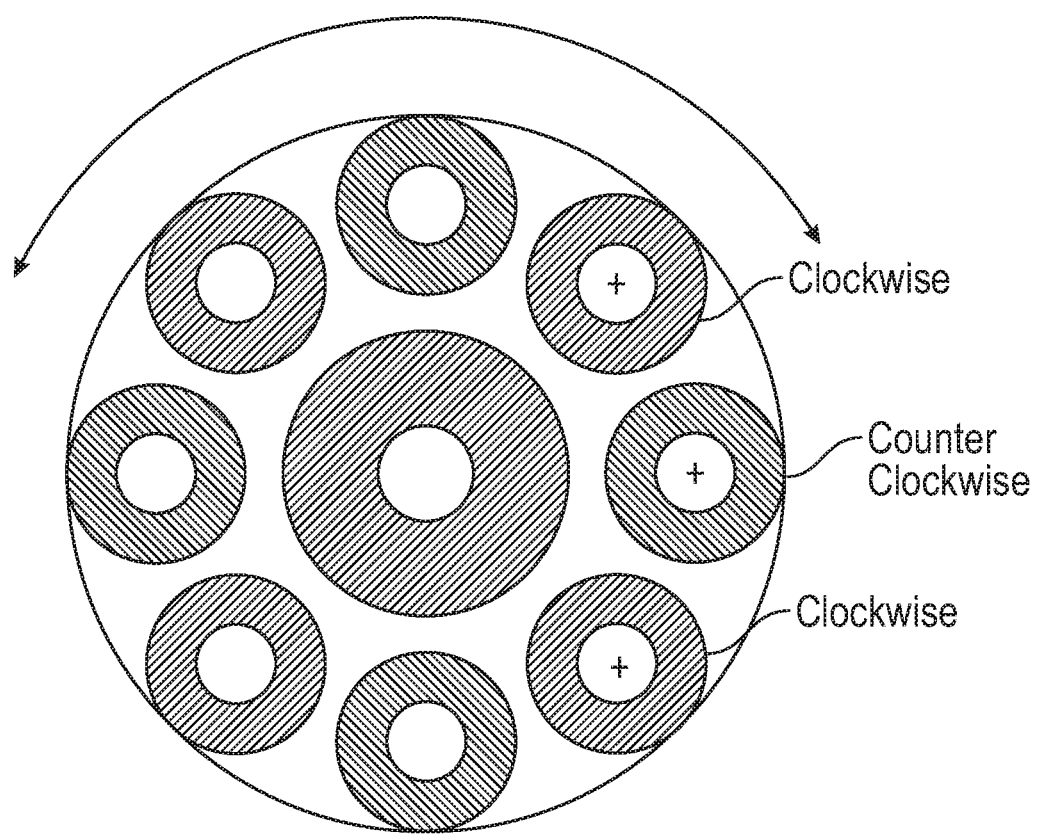
FIG. 16 shows a disc replacement in which the clockwise- and counter-clockwise-wound coils are alternated.
Figure 17:
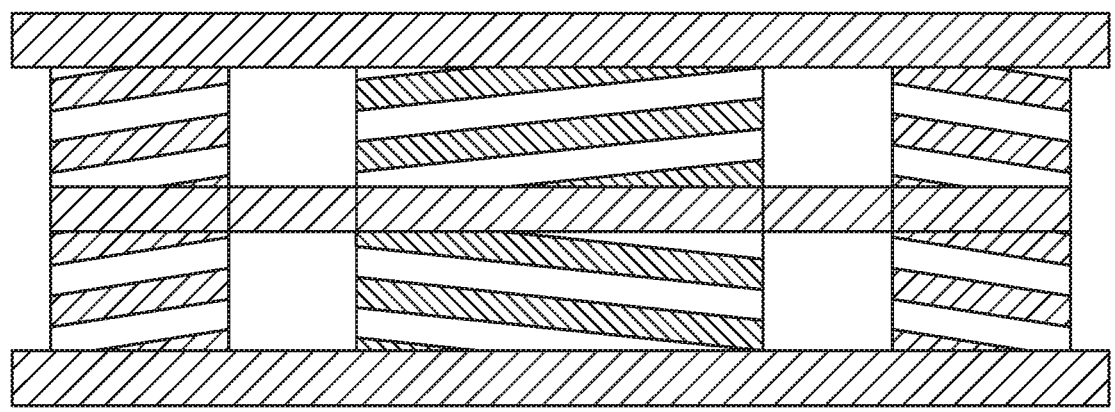
FIG. 17 illustrates a disc replacement having a first plurality of column springs below a second plurality of column springs.

According to some embodiments of the invention, at least one of the plurality of compressible column springs in the intervertebral disc replacement includes coils that are wound clockwise, and at least one of the plurality of compressible column springs includes coils that are wound counter-clockwise, as shown in FIG. 1. FIG. 16 shows a disc replacement in which the clockwise- and counter-clockwise-wound coils are alternated. This can enhance the stability of the disc replacement, and can prevent overrotation. FIG. 17 illustrates a disc replacement having a first plurality of column springs disposed below a second plurality of column springs. As shown in FIG. 17, the lower coils can be wound in the same direction as their upper counterparts, or can be would in the opposite direction.

Figure 18:
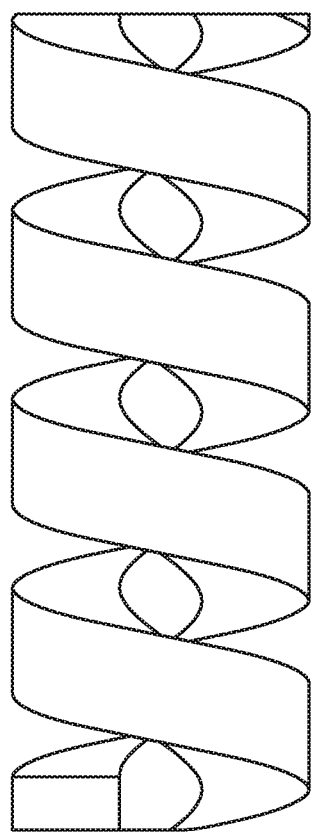
FIG. 18 shows a single compressible column spring according to some embodiments.

FIG. 18 shows a single compressible column spring according to some embodiments. When maximally compressed, the spring makes a continuous column. However, as described above, the embodiments of the invention are not limited to column springs having rectangular cross-sections like the one shown in FIG. 18. The edges of the coils may be shaved or rounded such that, when maximally compressed, the spring forms a column whose outer surface is uneven, different from that of a straight cylinder.

Figure 19:
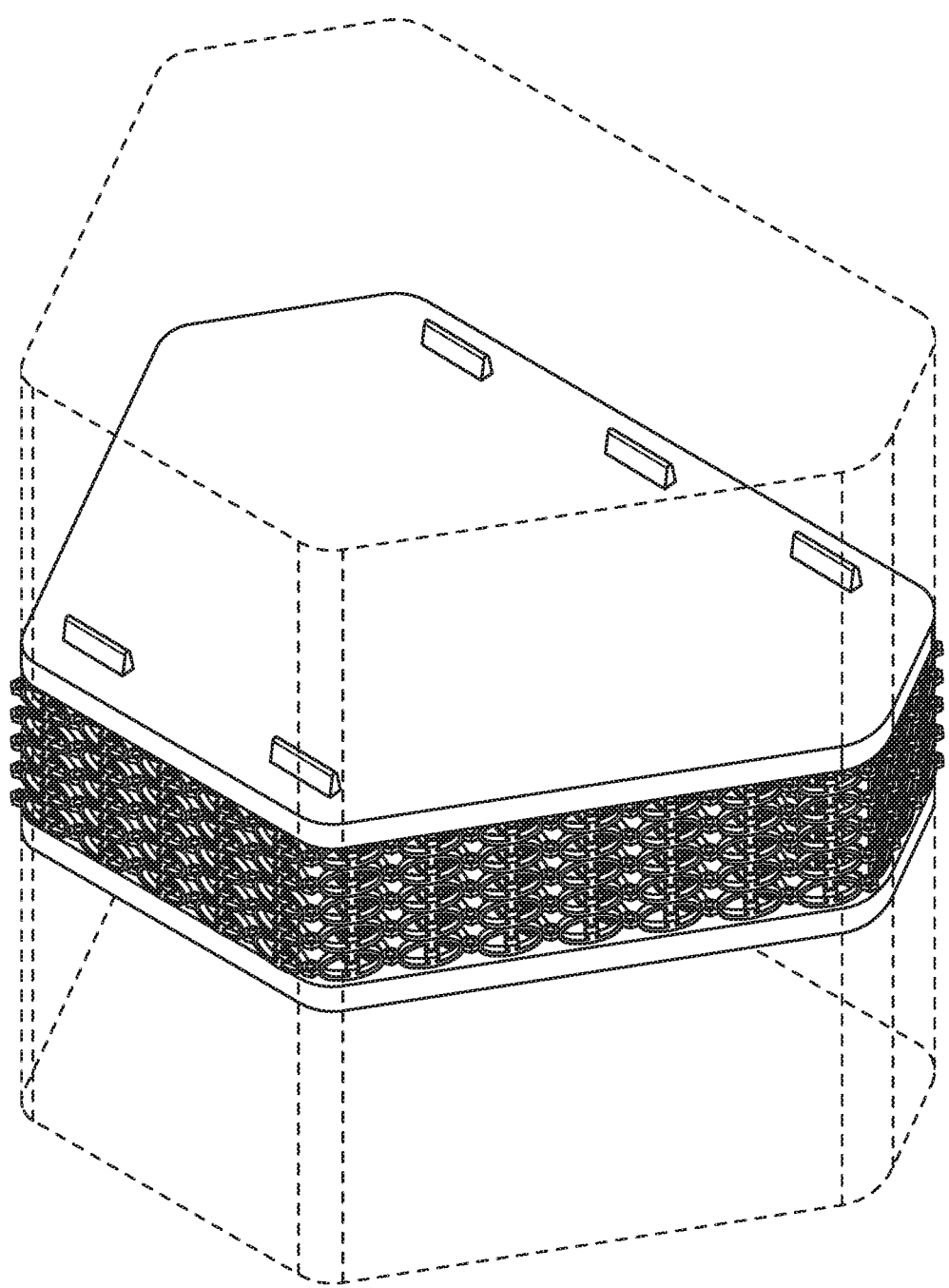
FIG. 19 shows an intervertebral disc replacement according to some additional embodiments, wherein the second layer comprising a compressible lattice.
Figure 20:
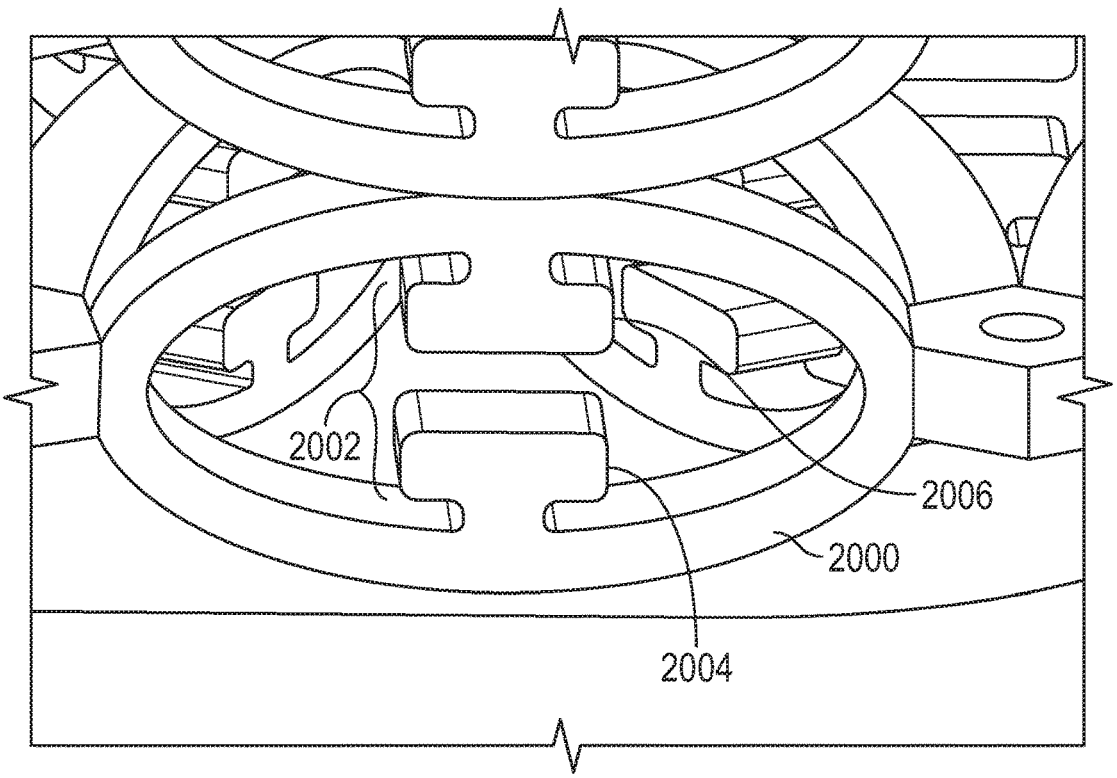
FIG. 20 shows a zoomed-in image of the compressible lattice according to some embodiments.

An intervertebral disc replacement according to some additional embodiments is shown in FIG. 19. The intervertebral disc replacement has a second layer comprising a compressible lattice. FIG. 20 shows a zoomed-in image of the compressible lattice according to some embodiments. The compressible lattice can be formed from layers of springs, or "struts." According to some embodiments, each strut 2000 has an O-like shape that can be compressed, thereby reducing the height of the strut, and can expand and/or return to its original state depending upon the forces being applied. For example, the struts can be of a shape-memory type so that when the compressive forces are removed, the struts return to their original position. Each strut can further comprise a stopper 2002. The stopper 2002 can be any mechanism that limits the extent to which the strut 2000 can be compressed, thereby preventing mechanical failure of the strut 100 due to excessive compression. The stoppers thus provide an elastic limit so that the struts do not fatigue or fracture. According to some embodiments, the stopper 2002 comprises two T-like features, an upright T-like feature 2004, and an inverted T-like feature 2006, disposed within the O-like strut 2000. When the strut 2000 is compressed, the T-like features 2004, 2006 are brought nearer to each other. The compression continues until the two T-like features 2004, 2006 come into contact with one another. The features prevent the strut from further compressing, providing a minimum displacement between the top and bottom layers of the disc replacement. The elasticity and/or shape memory of the struts can allow the device to accommodate expansion and compression. Advantageously, the lattice structure shown in the figures undergoes almost no lateral expansion when the disc replacement is compressed vertically.

According to some embodiments, the compressive quality of the lattice can be a result of the compressive design of each of the struts. The compressive lattice can be finely tuned to mimic the compressive characteristics of a native disc. For example, certain areas of the compressive lattice can be designed to be more or less resistant to compression, essentially changing the spring constant. One can thus design regions of the disc replacement known to experience greater forces to be less compliant, while less load-bearing areas can be more compressible.

Figure 21:
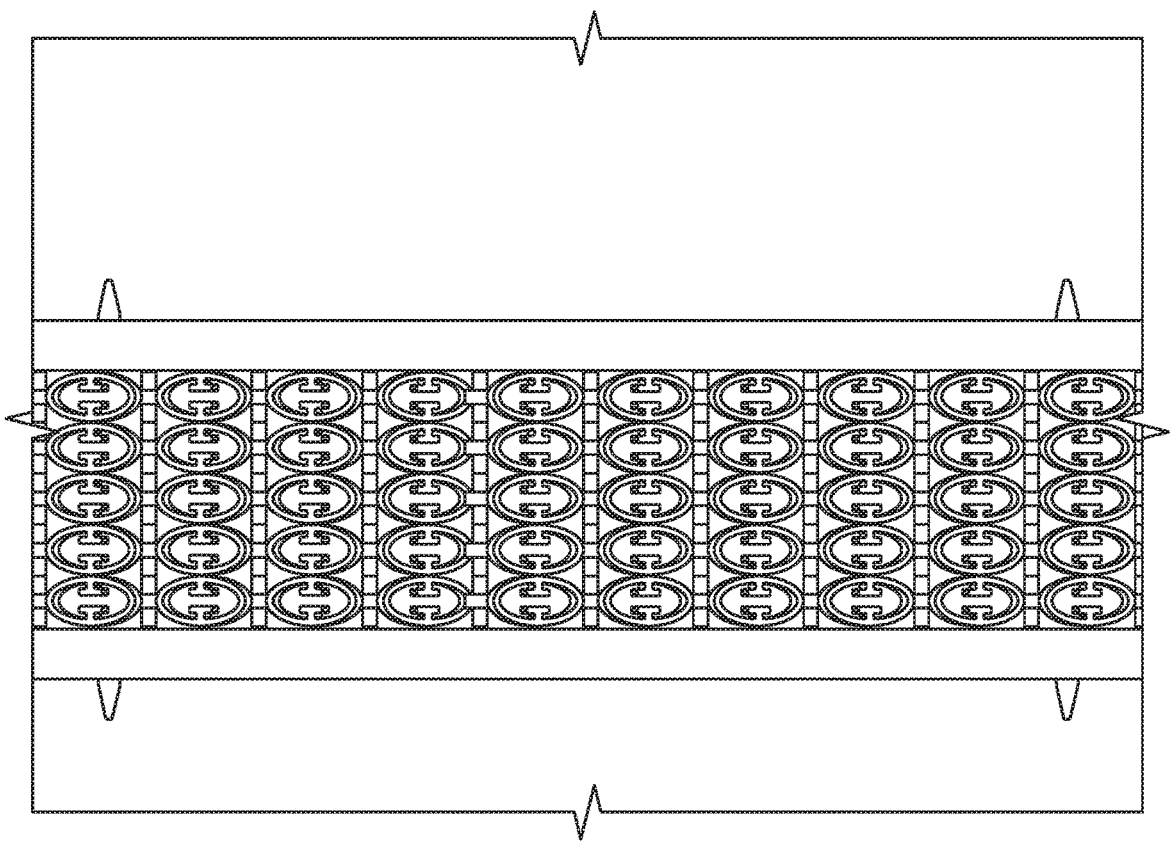
FIG. 21 shows a side view of an intervertebral disc replacement comprising a compressible lattice.
Figure 22:
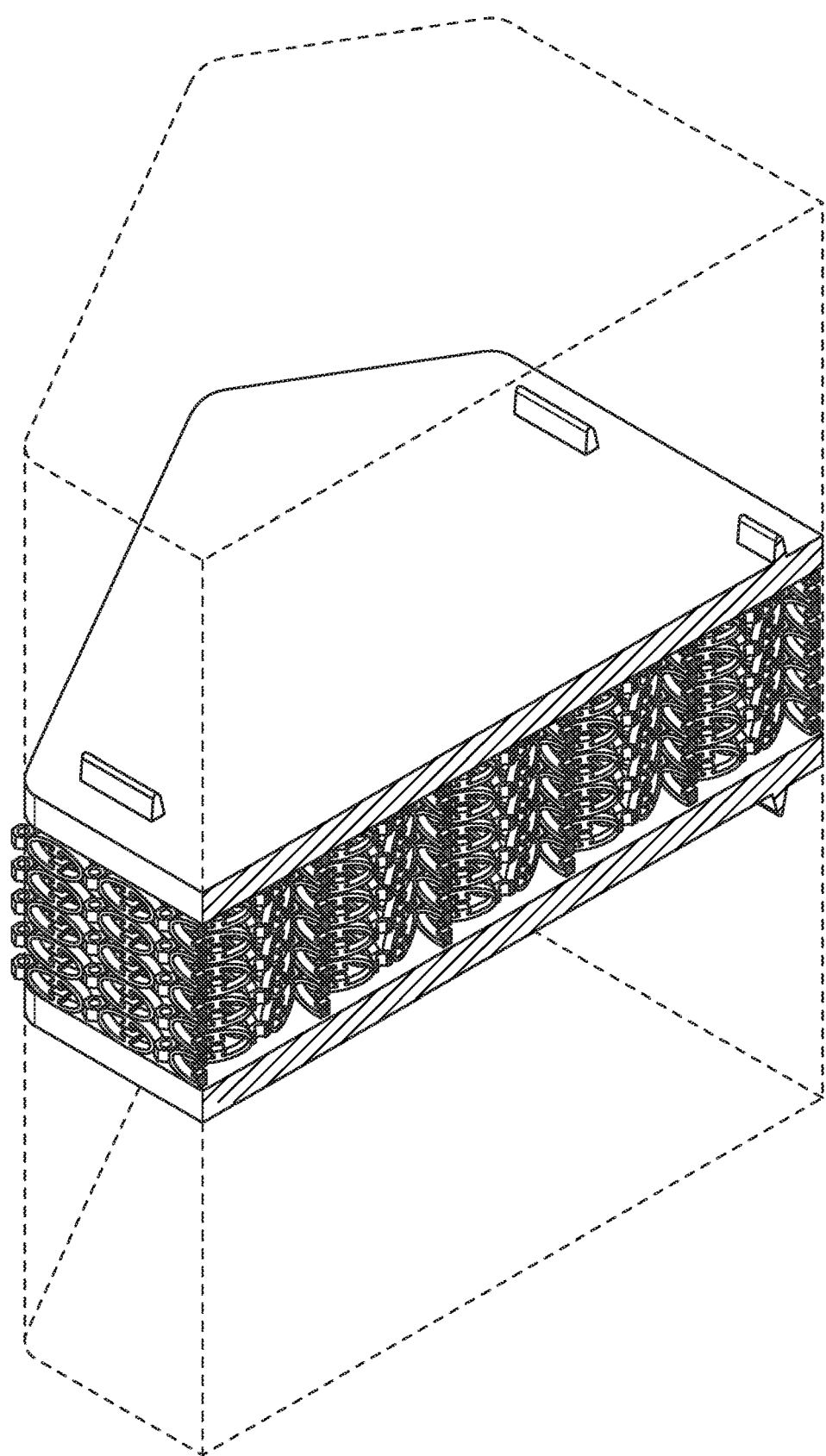
FIG. 22 shows a cross-section of an intervertebral disc replacement comprising a compressible lattice.
Figure 23:
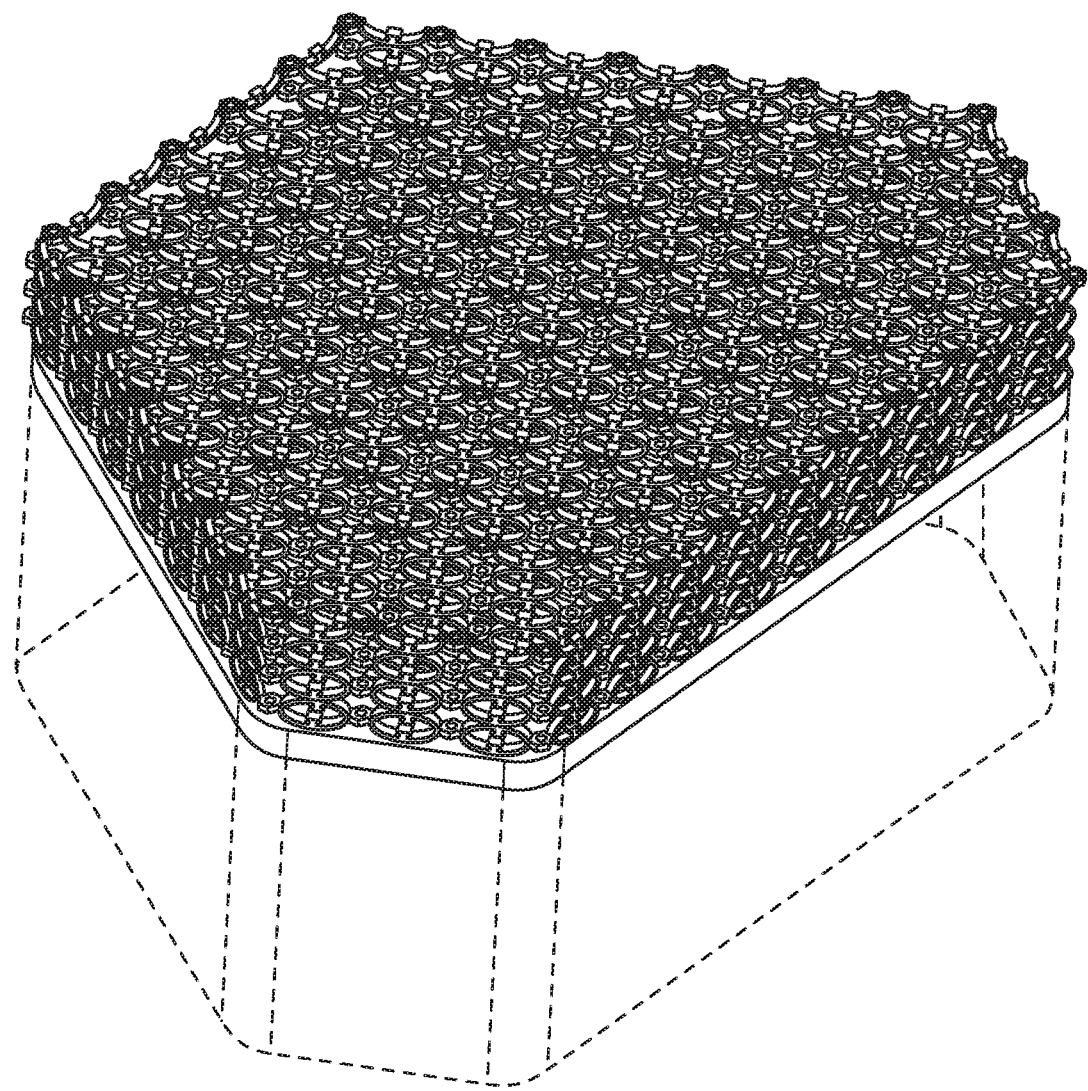
FIG. 23 shows the first and second layers of an intervertebral disc replacement comprising a compressible lattice.
Figure 24:
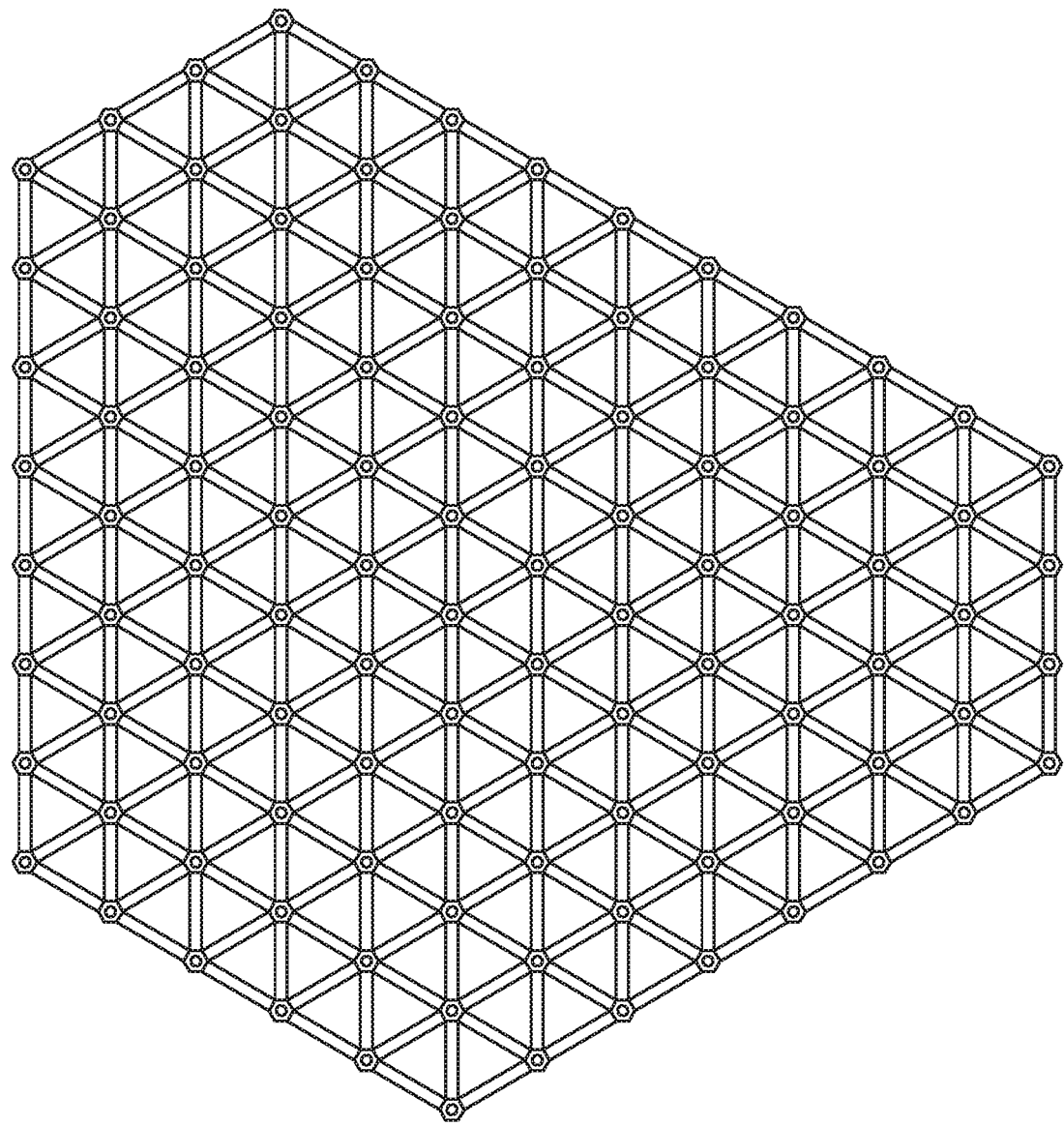
FIG. 24 shows a top view of the compressible lattice.

FIG. 21 shows a side view of an intervertebral disc replacement comprising a compressible lattice. FIG. 22 shows a cross-section of an intervertebral disc replacement comprising a compressible lattice. FIG. 23 shows the first and second layers of an intervertebral disc replacement comprising a compressible lattice. FIG. 24 shows a top view of the compressible lattice. According to some embodiments, the lattice has a repeating hexagonal structure. While the lattices shown in the figures have a regular, repeating structure, the shape and size of the individual elements can in fact be varied. For example, in some regions the lattice can be thicker to provide additional support and resistance to compression. The lattice is also not limited to the number of layers shown in the figures. The lattice could comprise more or fewer layers, and the struts could be made larger or smaller. For the lattice comprising column springs, the springs within the lattice may have different diameters and thicknesses, and the spacing between them may vary. These parameters may be adjusted such that different regions have different compressive and rotational qualities, allowing the disc replacement to mimic the movement of a native disc.

According to some embodiments of the invention, the intervertebral disc replacement is fabricated using 3D printing. For example, a powder-based 3D printer, such as a powder and laser-based 3D printer, can be used to form the first layer, the second layer comprising a plurality of column springs, and the third layer. The disc replacement can be formed as a single piece, or as multiple pieces that are then connected. According to some embodiments, the column springs are printed directly on top of the first layer, and the third layer is printed on top of the plurality of column springs. Similarly, for embodiments of the disc replacement having more than three layers, each layer can be printed directly on the layer below it. During the formation process, the disc replacement may also be inverted such that the layer that will be uppermost in the patient's body is printed first. According to some embodiments, the disc replacement comprises one or more of titanium, nitinol, cobalt chrome, high density polycarbonate, and any other material used for implants in the human body. Titanium can be advantageous because it is not magnetic or ferromagnetic, and is biocompatible. All biocompatible materials are contemplated in accordance with the principles of the invention.

According to some embodiments, the 3D printing process includes printing using multiple materials in a single disc. For example, the first and/or third layer may be printed using a first material, while the plurality of column springs is printed using a second material. The column springs themselves may comprise more than one material. For example, different materials may be used to vary the spring constant within a single column spring, or from one column spring to the next. Multiple materials may also be used to form the first layer and the third layer. The first layer may comprise different material(s) than the third layer according to some embodiments.

According to some embodiments of the invention, the disc replacement is formed using sintering. Sintering is the process of compacting and forming a solid mass of material by heat and/or pressure without melting it to the point of liquefaction. However, the embodiments of the invention are not limited to 3D printing and sintering, and other appropriate manufacturing methods may also be implemented.

Because the device can be 3D printed, its shape, as well as its compressive and rotational characteristics, can be patient-specific. For example, the surface area of the first and third layers may appear elliptical, kidney shaped, oval, or trapezoidal from a top-down view, while appearing scalloped or winged from a cross-sectional view, for example. The dimensions of the disc replacement are patient-specific, designed to match the size of the native disc, and meet the rotational, compressive, and load-bearing requirements of the native disc that will be replaced.

The design of the disc replacement may take into account data from an X-ray, a magnetic resonance image (MRI), or a computer tomography (CT) scan. The disc replacement may also be tailored in a patient specific manner taking into account the exact patient disc geometry from X-ray/MRI/CT, the disc level (each disc level requires different mechanical properties), the weight of the patient body portion above the disc, etc. Based on these factors, the disc replacement will be a patient specific disc in which the end plates and their angle, the disc replacement's volume, its springs geometry (both the individual construction of each spring and its resistance, as well as number of springs and their disposition along the disc area) are all tailored to meet the exact needs of the patient.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. Moreover, features described in connection with one embodiment of the invention may be used in conjunction with other embodiments, even if not explicitly stated above.

We claim:

1. A method of producing a patient-specific intervertebral disc replacement comprising a plurality of compressible springs, the method comprising the steps:
   a) obtaining data for a patient, the data comprising at least one of x-ray data, magnetic resonance imaging (MRI) data, computed tomography (CT) data, and the patient's body mass above the intervertebral disc replacement;
   b) determining a position of each compressible spring of the plurality of compressible springs and at least one spring constant of each compressible spring of the plurality of compressible springs, after step a), based on the obtained data to match patient-specific level positioning and movement needs;
   c) forming, using a powder-based 3D printer, after step b), a first portion of the intervertebral disc replacement, the first portion having a first surface for contacting a first vertebral bone;
   d) forming, using the powder-based 3D printer, after step c), on top of the first portion, a second portion comprising the plurality of compressible springs having the determined positions and the determined spring constants;
   e) forming, using the powder-based 3D printer, after step d), a third portion on top of the second portion, the third portion having a second surface for contacting a second vertebral bone; and
   f) removing, after step e), unbound powder from the plurality of compressible springs.

2. The method according to claim 1, wherein the determining the position of each compressible spring of the plurality of compressible springs and the at least one spring constant of each compressible spring of the plurality of compressible springs is further based on a disc level of the patient's native disc.

3. The method according to claim 1, wherein the determining the position of each compressible spring of the plurality of compressible springs and the at least one spring constant of each compressible spring of the plurality of compressible springs further includes determining positions and spring constants to reestablish normal lordosis or kyphosis.

4. The method according to claim 1, wherein the determining the position of each compressible spring of the plurality of compressible springs and the at least one spring constant of each compressible spring of the plurality of compressible springs further includes determining positions and spring constants to address preoperative sagittal plane deformity.

5. The method according to claim 1, wherein determining the at least one spring constant of each compressible spring of the plurality of compressible springs includes determining a single spring constant for each compressible spring of the plurality of compressible springs.

6. The method according to claim 1, wherein at least two of the compressible springs of the plurality of compressible springs have different spring constants.

7. The method according to claim 1, wherein determining the at least one spring constant of each compressible spring of the plurality of compressible springs includes determining two or more springs constants for at least one compressible spring of the plurality of compressible springs.

8. The method according to claim 1, wherein the compressible springs are column springs.

9. The method according to claim 8, wherein the at least one spring constant of a column spring is varied by varying at least one of a thickness, a height, or a pitch of coils of the column spring.

10. The method according to claim 1, wherein the first portion, the second portion, and the third portion form a monolithic structure.

11. The method according to claim 1, wherein each of the first portion, the second portion, and the third portion are formed from a single material.

12. The method according to claim 1, wherein forming the first portion and the third portion of the intervertebral disc replacement comprises forming at least one of the first portion and the third portion to match a size of the patient's native vertebra.

13. The method according to claim 12, wherein forming the first portion and the third portion of the intervertebral disc replacement further comprises forming at least one of the first portion and the third portion to match a shape of the patient's native vertebra.

14. The method according to claim 1, wherein forming the first portion and the third portion of the intervertebral disc replacement comprises forming at least one of the first portion and the third portion to have the first surface and the second surface that are not parallel.

15. The method according to claim 14, wherein an angle formed by the first surface and the second surface is determined based on the obtained data.

16. The method according to claim 1, wherein forming the first portion and the third portion of the intervertebral disc replacement comprises forming at least one of the first portion and the third portion to have a thickness that varies based on the obtained data.

17. The method according to claim 1, wherein forming the second portion of the intervertebral disc replacement comprises forming the second portion to have a thickness that varies.

18. The method according to claim 1, wherein forming the first portion and the third portion of the intervertebral disc replacement comprises forming the first portion and the third portion to have a thickness that is not constant, and
wherein forming the first portion, the second portion, and the third portion of the intervertebral disc replacement comprises forming the first portion, the second portion, and the third portion such that a distance between the first portion and the third portion varies.

19. The method according to claim 1, wherein each compressible spring of the plurality of compressible springs comprises a plurality of coils, wherein each coil has a cross-section, wherein the cross-section of each coil has a flat first surface and a flat second surface that is parallel to the flat first surface, wherein, when a compressible spring of the plurality of compressible springs is maximally compressed, the flat first surface and the flat second surface of adjacent coils contact each other, forming a continuous column without space between adjacent coils, and wherein a height of the continuous column defines a predetermined limit beyond which the intervertebral disc replacement cannot be compressed.

* * * * *